(12) United States Patent
West et al.

(10) Patent No.: US 6,685,730 B2
(45) Date of Patent: Feb. 3, 2004

(54) OPTICALLY-ABSORBING NANOPARTICLES FOR ENHANCED TISSUE REPAIR

(75) Inventors: Jennifer L. West, Pearland, TX (US); Rebekah Drezek, Houston, TX (US); Scott Sershen, San Francisco, CA (US); Nancy J. Halas, Houston, TX (US)

(73) Assignee: Rice University, Houston, TX (US)

( * ) Notice: Subject to any disclaimer, the term of this patent is extended or adjusted under 35 U.S.C. 154(b) by 0 days.

(21) Appl. No.: 10/254,233

(22) Filed: Sep. 25, 2002

(65) Prior Publication Data

US 2003/0093092 A1 May 15, 2003

Related U.S. Application Data

(60) Provisional application No. 60/325,038, filed on Sep. 26, 2001.

(51) Int. Cl.$^7$ ............................................. A61N 5/067
(52) U.S. Cl. ......................... 607/89; 607/88; 607/100
(58) Field of Search ........................... 606/2, 4–9, 27; 428/403; 424/497; 128/898

(56) References Cited

U.S. PATENT DOCUMENTS

| | | |
|---|---|---|
| 4,633,870 A | 1/1987 | Sauer |
| 4,672,969 A | 6/1987 | Dew |
| 4,854,320 A | 8/1989 | Dew et al. |
| 4,877,647 A | 10/1989 | Klabunde |
| 5,002,051 A | 3/1991 | Dew et al. |
| 5,118,293 A | 6/1992 | Levy |
| 5,152,759 A | 10/1992 | Parel et al. |
| 5,156,613 A | 10/1992 | Sawyer |
| 5,209,776 A | 5/1993 | Bass et al. |
| 5,281,211 A | 1/1994 | Parel et al. |
| 5,290,272 A | 3/1994 | Burstein et al. |
| 5,292,362 A | 3/1994 | Bass et al. |
| 5,330,974 A | 7/1994 | Pines et al. |
| 5,334,191 A | 8/1994 | Poppas et al. |
| 5,336,221 A | 8/1994 | Anderson |
| 5,354,323 A | 10/1994 | Whitebook |

(List continued on next page.)

OTHER PUBLICATIONS

Zeebregts, C.J., et al., *Non–suture methods of vascular anastomosis*, Br J Surg. Mar. 2003;90(3):261–71.

Schalow, E.L., et al., *Laser tissue soldering: applications in the genitourinary system*, Curr Urol Rep. Feb. 2003;4(1):56–9.

Capon, A., et al., *Can thermal lasers promote skin wound healing?* Am J Clin Dermatol. 2003;4(1):1–12.

Talmor, M., et al., *Laser tissue welding: a biotechnological advance for the future*, Arch Facial Plast Surg. 2001 Jul.–Sep.;3(3):207–13.

(List continued on next page.)

*Primary Examiner*—Roy D. Gibson
(74) *Attorney, Agent, or Firm*—Fulbright & Jaworski L.L.P.

(57) ABSTRACT

This invention is generally in the field of improved methods for the localized delivery of heat and the use thereof for the repair of tissue. The method involves localized induction of hyperthermia in tissue or materials by delivering nanoparticles to the tissue or materials and exposing the nanoparticles to an excitation source under conditions wherein they emit heat. The generation of heat effects the joining of the tissue or materials.

64 Claims, 3 Drawing Sheets

U.S. PATENT DOCUMENTS

| | | | |
|---|---|---|---|
| 5,364,389 A | | 11/1994 | Anderson |
| 5,409,479 A | | 4/1995 | Dew et al. |
| 5,409,481 A | | 4/1995 | Poppas et al. |
| 5,411,730 A | | 5/1995 | Kirpotin et al. |
| 5,498,259 A | | 3/1996 | Mourant et al. |
| 5,507,744 A | | 4/1996 | Tay et al. |
| 5,540,677 A | | 7/1996 | Sinofsky |
| 5,552,452 A | | 9/1996 | Khadem et al. |
| 5,571,216 A | | 11/1996 | Anderson |
| 5,591,157 A | | 1/1997 | Hennings et al. |
| 5,605,887 A | | 2/1997 | Pines et al. |
| 5,611,794 A | | 3/1997 | Sauer et al. |
| 5,612,050 A | | 3/1997 | Rowe et al. |
| 5,642,997 A | | 7/1997 | Gregg, II et al. |
| 5,662,643 A | | 9/1997 | Kung et al. |
| 5,669,934 A | | 9/1997 | Sawyer |
| 5,713,891 A | | 2/1998 | Poppas |
| 5,725,522 A | | 3/1998 | Sinofsky |
| 5,749,895 A | | 5/1998 | Sawyer et al. |
| 5,810,810 A | | 9/1998 | Tay et al. |
| 5,814,040 A | | 9/1998 | Nelson et al. |
| 5,824,015 A | | 10/1998 | Sawyer |
| 5,827,265 A | | 10/1998 | Glinsky et al. |
| 5,849,035 A | | 12/1998 | Pathak et al. |
| 5,925,078 A | | 7/1999 | Anderson |
| 6,033,401 A | | 3/2000 | Edwards et al. |
| 6,087,552 A | | 7/2000 | Gregory |
| 6,165,440 A | * | 12/2000 | Esenaliev .................. 424/1.11 |
| 6,176,871 B1 | | 1/2001 | Pathak et al. |
| 6,211,335 B1 | | 4/2001 | Owen et al. |
| 6,221,068 B1 | * | 4/2001 | Fried et al. .................... 606/8 |
| 6,248,117 B1 | | 6/2001 | Blatter |
| 6,258,872 B1 | | 7/2001 | Stedronsky |
| 6,323,037 B1 | | 11/2001 | Lauto et al. |
| 6,375,634 B1 | * | 4/2002 | Carroll ......................... 604/19 |
| 6,391,049 B1 | | 5/2002 | McNally et al. |
| 6,398,797 B2 | | 6/2002 | Bombard et al. |
| 6,428,811 B1 | | 8/2002 | West et al. |
| 6,530,944 B2 | * | 3/2003 | West et al. .................... 607/88 |
| 6,551,334 B2 | | 4/2003 | Blatter et al. |
| 6,562,059 B2 | | 5/2003 | Edwards et al. |
| 6,569,173 B1 | | 5/2003 | Blatter et al. |
| 6,576,685 B2 | | 6/2003 | Stedronsky |

OTHER PUBLICATIONS

Poppas, D.P., et al., *Laser tissue welding: a urological surgeon's perspective*, Haemophilia. Jul. 1998;4(4):456–62.

Werker, P.M., et al., *Review of facilitated approaches to vascular anastomosis surgery*, Ann Thorac Surg. Jun. 1997;63(6 Suppl):S122–7.

Vangsness, C.T., Jr. *Use of lasers for meniscal repair*, Clin Sports Med. Jul. 1996; 15(3):a531–5.

Uzzo, R.G., et al., *Genitourinary reconstructive surgery utilizing laser tissue welding*, Tech Urol. 1995 Summer;1(2):55–61.

Eden, C.G., *Alternative techniques for laparoscopic tissue anastomosis in the retroperitoneum*, Endosc Surg Allied Technol. Feb. 1995;3(1):27–32.

Manovsky, T., et al., *Laser(–assisted) nerve repair. A review.* Neurosurg Rev. 1995;18(4):225–35.

Bass, L.S., et al, *Laser tissue welding: a comprehensive review of current and future clinical applications*, Lasers Surg Med. 1995;17(4):315–49.

Bhatta, K.M., et al., *Lasers in urology*, Lasers Surg Med. 1995;16(4):312–30.

Poppas, D.P., et al., *Laser tissue welding in urologic surgery*, Urology. 1994 Feb.;43(2):143–8.

Nemeth, A.J., *Lasers and wound healing*, Dermatol Clin. Oct. 1993 ;11(4):783–9.

Dew, D.K., et al., *Tissue repair using lasers: a review*, Orthopedics. May 1993;16(5):581–7.

Abelow, S.P., *Use of lasers in orthopedic surgery: current concepts*, Orthopedics. May 1993;16(5):551–6.

Colvard, M.D., et al., *Future directions of lasers in dental medicine*, Curr Opin Periodontol. 1993;144–50.

McCue, J.L., et al., *Sutureless intestinal anastomoses*, Br J. Surg Nov. 1991;78(11):1291–6.

Schlossberg, S.M., et al., *Tissue welding with lasers*, Semin Urol. 1991 Aug.;9(3):206–9.

Fried, M.P., et al., *Head and neck applications of the milliwatt laser*, Lasers Surg Med. 1987;7(1):46–50.

Bailes, J.E., et al., *Review of tissue welding applications on neurosurgery*. Microsurgery. 1987;8(4):242–4.

Kirsch, A.J., et al., *Laser welding with albumin–based solder: experimental full–tubed skin graft urethroplasty*, Lasers Surg Med. 1996;18(3):225–30.

White, R.A., *Technical frontiers for the vascular surgeon: laser anastomotic welding and angioscopy–assisted intraluminal instrumentation*, J Vasc Surg. Apr. 1987;5(4):673–80.

Tang, J., et al, *A comparison of Cunyite and Fosterite NIR tunable laser tissue welding using native collagen fluorescence imaging*, J Clin Laser Med Surg. Jun. 2000;18(3):117–23.

Ott, B., et al, *Comparative in vitro study of tissue welding using a 808 nm diode laser and a Ho–YAG laser*, Lasers Med Sci. 2001;16(4):260–6.

Zilker, Z., et al., *Carbon dioxide laser and silver halide infrared transmitting fibers for tympanoplasty: an expiremental animal model*, Otolaryngol Head Neck Surg. Sep. 2001;125(3):157–60.

Lauto, A., et al., *Carotid artery anastomosis with albumin solder and near infrared lasers: a comparative study*, Lasers Surg Med. 2001;28(1):50–5.

Fried, N.M., et al., *Laser skin welding: in vivo tensile strength and wound healing results*, Lasers Surg Med. 2000;27(1):55–65.

Fried, N.M., et al., *Radiometric surface temperature measurements during dye–assisted laser skin closure: in vitro and in vivo results*, Lasers Surg Med. 1999;25(4):291–303.

Lauto, A., et al., *Two–layer film as a laser soldering biomaterial*, Lasers Surg Med. 1999;25(3):250–6.

McNally, K.M., et al., *Photothermal effects of laser tissue soldering*, Phys Med. Biol. Apr. 1999;44(4):983–1002.

Massicote, J.M., et al., *Effects of endogenous absorption in human albumin solder for actue laser wound closure*, Lasers Surg Med. 1998;23(1):18–24.

Small, W., IV, et al., *Dye–enhanced protein solders and patches in laser–assisted tissue welding*, J Clin Laser Med Surg. 1997;15(5):205–8.

Tang, J.R., et al., *Mechanism of aneurysm formation after 830–nm diode–laser–assisted microarterial anastomosis*, J Clin Laser Med Surg. 1997;15(4):175–9.

* cited by examiner

OPTICALLY-ABSORBING NANOPARTICLES FOR ENHANCED TISSUE REPAIR

This application claims priority to U.S. Provisional Application Ser. No. 60/325,038, filed Sep. 26, 2001. U.S. Pat. No. 6,344,272; U.S. application Ser. No. 09/779,677, filed Feb. 28, 2001; U.S. application Ser. No. 09/038,377, filed Apr. 10, 1998; U.S. Application Ser. No. 60/222,437, filed Aug. 1, 2000; and PCT/US00/19268, filed Jul. 14, 2000 are specifically and fully incorporated by reference herein.

BACKGROUND OF THE INVENTION

Laser tissue welding refers to techniques by which tissues may be joined in response to exposure to light and the subsequent generation of heat. The goal of these techniques is the rapid joining of tissues with high tensile strength across the union, union throughout the depth of the targeted tissue, a minimum of scar tissue formation, and minimal damage to surrounding tissue. These techniques may also be beneficial in a number of minimally invasive surgical techniques. Laser tissue repair is under investigation or in use in many surgical disciplines for procedures such as closure of skin wounds, vascular anastamosis, occular repair, nerve repair, cartilage repair, and liver repair. Currently, laser tissue repair is accomplished either through welding, apposing two tissue surfaces then exposing to laser radiation to heat the tissues sufficiently to join them, or through soldering, wherein an exogenous material such as a protein or synthetic polymer is placed between two tissue surfaces to enhance joining of the tissues upon exposure to laser radiation. Temperatures greater than 50° C. can induce tissue union. This is believed to be induced by the denaturation of proteins and the subsequent entanglement of adjacent protein chains.

In traditional approaches, tissue welding is accomplished when laser light is absorbed by tissue components such as water or hemoglobin, producing sufficient heat to cause denaturation of collagens and other proteins with subsequent entanglement of adjacent protein chains (Guthrie, 1991). The laser light used in this traditional approach does not discriminate between the wound surface and other tissue. As a result, the success of laser tissue welding has been limited because of (1) the generation of superficial welds with poor mechanical integrity as a result of poor optical penetration and (2) excessive damage to adjacent tissues (Bass, et al. 1995; DeCoste, et al., 1992; Robinson, et al., 1987).

Given these limitations, focus has turned to the investigation of exogenous materials to facilitate the transfer of heat to enable wound closure. The exogenous materials used to facilitate laser tissue welding fall into two categories: those selected to preferentially convert light to heat and those selected to facilitate wound closure and healing. Light absorbing materials currently employee include indocyanine green (U.S. Pat. No. 6,221,068, Bass, et al., 1992; Cooper, et al., 2001; and McNally, et al., 1999), India ink (Fried, et al., 2000), and carbon black (Lauto, et al., 2001). Other examples of the use of chromophores, either alone or in combination with other components, include the works of Birch, Cooper, McNally, Sorg and others. The second class of compounds, commonly referred to as solders, has the primary task of facilitating tissue bonding and healing, and is principally used in conjunction with light-absorbing materials as described above. Ranging from viscous solutions to semi-solid pastes, solders are typically made from biocompatible materials like albumin (Wider, et al., 2001; McNally, et al., 2000; Menovsky, et al., 2001; Lauto, et al., 2001; Zuger, et al., 2001; Bleustein, et al., 2000; Poppas, et al., 1993), albumin with hyaluronic acid (Kirsch, et al., 1997; Ott, et al., 2002), fibrinogen (Wider, et al., 1991), collagen (Small, et al., 1997), cellulose (Bleustein, et al., 2000) or chitosan (Lauto, et al., 2001). From these studies it can be ascertained that the primary duties of a solder are to keep dyes immobile when applied in vivo and to provide a sealant across uneven wound edges.

The use of the nanoparticles of the present invention over chemical chromophores is desirable due to the ability to achieve stronger optical absorption and heat generation, the opportunity for tunable absorption, potentially better biocompatibility, and the ability to better target binding to specific cells or tissues.

In many applications, it is desirable to target cells and tissue for localized heating. The therapeutic effects range from the destruction of cancerous cells and tumors, to the therapeutic or cosmetic removal of benign tumors and other tissue. Techniques which effect precise localized heating and illumination would allow one to enjoy therapeutic and diagnostic benefits, while minimizing the collateral damage to nearby cells and tissue. It is desirable that such techniques be amenable to both in vitro and in vivo therapeutic and diagnostic applications of induced hyperthermia and imaging, respectively, of cells and tissue.

A potentially useful in vivo application of such a technique has been recognized for cancer treatment. For example, metastatic prostate cancer is a leading cause of mortality in American men. Estimates indicate that greater than one in every eleven men in the U.S. will develop prostate cancer. Accurate determination of the extent of local disease is often difficult. Methods for accurately detecting localized prostate disease are greatly needed. In addition, localized prostate cancer is generally treated with either radical prostatectomy or radiation therapy. Both of these procedures are plagued by significant morbidity. Minimally invasive treatment strategies with low associated morbidity are made feasible through such applications and could potentially dramatically improve prostate cancer therapy.

A number of techniques have been investigated to direct therapeutic agents to tumors. These have included targeting of tumor cell surface molecules, targeting regions of activated endothelium, utilizing the dense and leaky vasculature associated with tumors, and taking advantage of the enhanced metabolic and proteolytic activities associated with tumors. Antibody labeling has been used extensively to achieve cell-selective targeting of therapeutic and diagnostic agents. A number of approaches have been taken for antibody-targeting of therapeutic agents. These have included direct conjugation of antibodies to drugs such as interferon-alpha (Ozzello, et al., 1998), tumor necrosis factor (Moro, et al., 1997), and saporin (Sforzini, et al., 1998). Antibody conjugation has also been used for tumor-targeting of radioisotopes for radioimmunotherapy and radioimmunodetection (Zhu, et al., 1998). Currently, there is a commercial product for detection of prostate cancer (ProstaScint) that is an antibody against prostate-specific membrane antigen conjugated to a scintigraphic target (Gregorakis, et al., 1998).

The nanoparticles that are the subject of this invention are amenable to these types of targeting methodologies. Examples of such have been described previously in the following copending patent applications: U.S. application Ser. Nos. 09/779,677 and 09/038,377, and international application PCT/US00/19268, which are fully incorporated by reference as if expressly disclosed herein. The nanoparticle surfaces can easily be modified with antibodies, peptides, or other cell-specific moieties. The utility of these nanoparticles in the localized treatment of disease is a consequence of their photothermal properties. It has been shown that elevated temperatures are useful in joining tissue. (Lobel, et al., 2000; Fried, et al., 1999). Judicious placement of the nanoparticles to the area to be treated, followed by the proper excitation results in a localized heating which forms the basis of the various nanoparticle treatment strategies demonstrated to date.

We now demonstrate that nanoparticles that strongly absorb light corresponding to the output of a laser are useful for another therapeutic application, namely as enhancing agents for laser tissue welding procedures. Specifically, gold-silica nanoshells are designed to strongly absorb light at 820 nm, matching the output of the diode laser used in these experiments. The nanoshells are coated onto the surfaces of two pieces of tissue at the site where joining was desired. Upon exposure to the diode laser, the tissue surfaces are joined when they had first been treated with nanoshells but are not joined under these illumination conditions without nanoshell treatment. Absorptive nanoparticles, such as metal nanoshells, may be coated onto tissue surfaces or may be incorporated into a tissue solder formulation. The nanoparticles offer tunable optical absorption to allow facile matching of nanoparticle absorption to the output of various commercial lasers. Additionally, the technique affords methods to minimize tissue damage by using the least harmful wavelengths of light and/or lower powered light sources.

SUMMARY OF THE INVENTION

In the preferred embodiment, a method of joining tissue comprises delivering nanoparticles that absorb light at one or more wavelengths to the tissue and, exposing the nanoparticles to light at one or more wavelengths that are absorbed by the nanoparticles. In the preferred embodiment, the light is laser light although it may alternatively be non-laser radiation. It is also preferred that the nanoparticles used be nanoshells. In a specific embodiment, the nanoparticles are metal nanoshells. Alternatively, the nanoparticles are metal colloids, such as gold colloid or silver colloid. In another embodiment, the nanoparticles may be fullerenes. In the preferred embodiment, all of the nanoparticles are of the same composition; however alternatively, the nanoparticles may be of more than one composition. In the preferred embodiment, the light is infrared light; in alternative embodiments, the light may be visible or ultraviolet or any combination of infrared, visible, or ultraviolet light. In a specific embodiment, the light is red to near-infrared and is in the wavelength range of 600–2000 nm. In a preferred embodiment, the light is near-infrared light and is in the wavelength range of 700–1200 nm. Most preferably, the light is in the wavelength range of 750–1100 nm. The nanoparticles have dimensions of between 1 and 5000 nanometers. In the preferred embodiment, the nanoparticles have dimensions of between 1 and 1000 nanometers.

In a specific embodiment, at least a portion of the nanoparticles is mixed with one or more proteins. Specific embodiments of protein/nanoparticles systems include nanoparticles mixed with albumin, fibrinogen, collagen, elastin, fibronectin, laminin, chitosan, fibroblast growth factor, vascular endothelial cell growth factor, platelet-derived growth factor, epidermal growth factor, or insulin-like growth factor or combinations thereof. Alternatively, at least a portion of the nanoparticles may be mixed with one or more polymers. Specific embodiments of polymer/nanoparticle systems include nanoparticles mixed with polyethylene, polyethylene glycol, polystyrene, polyethylene terephthalate, polymethyl methacrylate, or combinations thereof. In another embodiment, at least a portion of the nanoparticles is mixed with one or more polymers and one or more proteins. In a specific embodiment, at least a portion of the nanoparticles is bound to a chemical moiety. In a specific embodiment, at least a portion of the nanoparticles is bound to an antibody.

In another embodiment of the invention, a method of joining tissue to non-tissue material comprises delivering a first set of nanoparticles that absorb light at one or more wavelengths to tissue, delivering a second set of nanoparticles that absorb light at one or more wavelengths to non-tissue material, and exposing the first set of said nanoparticles and the second set of nanoparticles to light at one or more wavelengths that are absorbed by the first set of nanoparticles and the second set of nanoparticles. In the preferred embodiment, the sets of nanoparticles are of the same composition. Alternatively, the sets of nanoparticles may be of different composition. In the preferred embodiment, the nanoparticles in the tissue and non-tissue absorb light at at least one common wavelength. Alternatively, they may absorb at different wavelengths. In the preferred embodiment, both sets of nanoparticles heat up simultaneously, thereby exhibiting the same heating profile. In alternative embodiments, the heating profiles may be different. In specific embodiments, one or both of the sets of nanoparticles are mixed with protein, polymer or a combination thereof. In the preferred embodiment, the light used is laser light, however, in an alternative embodiment, the light may be non-laser radiation. In a specific embodiment, the non-tissue is a medical device. In another specific embodiment, the non-tissues comprise engineered tissue.

In a specific embodiment of the present invention, a method for reducing wrinkles or other cosmetic defects such as stretch marks in tissue comprises delivering nanoparticles that absorb light at one or more wavelengths to the tissue and exposing said nanoparticles to light at one or more wavelengths that are absorbed by the nanoparticles. In other specific embodiments, methods for cosmetic or therapeutic laser resurfacing of tissue are used.

In another embodiment of the present invention, a method of heating tissue comprises delivering nanoparticles that absorb light at one or more wavelengths to the tissue and exposing the nanoparticles to light at one or more wavelengths that are absorbed by the nanoparticles. Nanoparticles may be delivered to the tissue in a formulation containing a protein or polymer. In a specific embodiment of the invention, tissue is ablated by the method. In another embodiment, coagulation of blood is induced by the method.

In another embodiment of the invention, a method of joining non-tissue materials comprises delivering nanoparticles that absorb light at one or more wavelengths to one or more of the materials, exposing said nanoparticles to light at one or more wavelengths that are absorbed by the nanoparticles. Nanoparticles may also be embedded within one or both non-tissue materials. In a specific embodiment, the non-tissue materials are polymers, such as polyethylene, polystyrene, polyethylene terephthalate, or polymethyl methacrylate. In this application, nanoparticles are intended to absorb light and convert it to heat in order to raise the temperature of the material to near or above the melting temperature. This increases the mobility of polymer chains, allowing chains from the adjacent materials to become entangled and for the materials to become mechanically interdigitated, thus forming a union between the two materials. Ideally, the nanoparticles would absorb light at a wavelength where absorption of light by the polymer is low so that heating will be localized to the region where nanoparticles are present. This can minimize the appearance of the joint between the two materials. Additionally, such an approach can minimize the size of the joint between two materials, which may be advantageous in microfabrication or other fabrication processes.

In a preferred embodiment, there is a method of joining tissue comprising the steps of delivering nanoshells to the tissue, the nanoshells having a light wavelength extinction maximum between 750 and 1100 nanometers, and exposing the nanoshells to light at wavelengths between 750 and 1100 nanometers.

In a specific embodiment of the method, at least a portion of said nanoshells is mixed with one or more proteins. In another specific embodiment, the one or more proteins is selected from the group consisting of albumin, fibrinogen, collagen, elastin, fibronectin, laminin, chitosan, fibroblast growth factor, vascular endothelial cell growth factor, platelet-derived growth factor, epidermal growth factor, or insulin-like growth factor and combinations thereof.

DETAILED DESCRIPTION OF THE INVENTION

Figure 1:
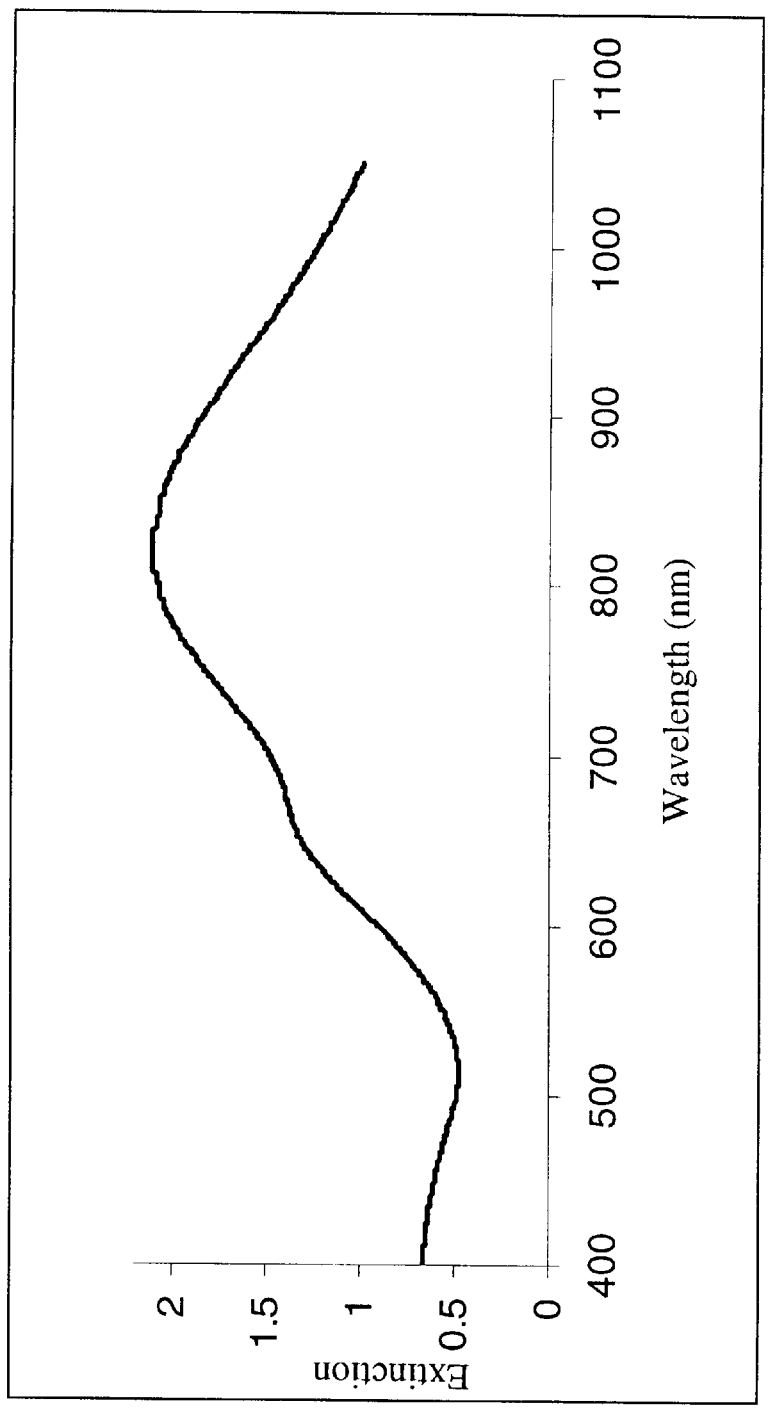
FIG. 1 is an absorbance spectrum of the gold-silica nanoshells used in the laser tissue welding of Example 3.

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "targeted" as used herein encompasses the use of antigen-antibody binding, ligand-receptor binding, and other chemical and/or biochemical binding interactions to direct the binding of a chemical species to a specific site.

As used herein, "light" means electromagnetic radiation, which includes but is not limited to infrared, visible, and ultraviolet radiation.

As used herein "delivering" nanoparticles to a location is defined as effecting the placement of the nanoparticles attached to, next to, or sufficiently close to the location such that any heat generated by the nanoparticles is transferred to the location. "Delivering" may be targeted or non-targeted as the term "targeted" is used herein.

"Nanometer" is $10^{-9}$ meter and is used interchangeably with the abbreviation "nm."

As used herein, "nanoparticle" is defined as a particle having dimensions of from 1 to 5000 nanometers, having any size, shape or morphology. For example, they may be metal colloids such as gold colloid or silver colloid. The nanoparticles may be fullerenes which are available in both nanosphere and nanotube structures.

As used herein, "nanoshell" is a nanoparticle having a discrete dielectric or semiconducting core section surrounded by one or more conducting shell layers. A "nanoshell" is a subspecies of nanoparticles characterized by the discrete core/shell structure.

As used herein, "nanoparticle" means one or more nanoparticles. As used herein, "nanoshell" means one or more nanoshells. As used herein, "shell" means one or more shells.

As used herein, "non-tissue" is defined as any material that is not human or animal tissue.

As used herein, the abbreviation "IR" means infrared generally, the abbreviation "NIR" means near-infrared, the abbreviation "UV" means ultraviolet, and the abbreviation "VIS" means visible. All of these terms retain their common meaning in the art.

As used herein, "localized" means substantially limited to a desired area with only minimal, if any, dissemination outside of such area.

In an important embodiment of the present invention, the nanoparticles administered to an animal using standard methods. Animals that may be treated using the method of the invention include, but are not limited to humans, cows, horses, pigs, dogs, cats, sheep goats, rabbits, rats, mice, birds, chickens or fish.

A method to repair tissue for therapeutic applications has been developed. Such repair envisions the joining of tissue with other tissue or tissue with non-tissue material. The technique involves the use of nanoparticles which effect a localized heating when exposed to an excitation source which is typically light and more typically laser light, the localized heating effects tissue repair. The nanoparticles of the present invention have dimensions of between 1 and 5000 nanometers. The excitation light used in typically NIR, although other excitation may be used such as the rest of the IR spectrum, UV, and VIS or combinations thereof. Typically, the light is in the wavelength range of 600–2000 nm; ideally, it is in the range of 750–1100 nm. The particles are ideally of nanometer-scale dimensions and are preferably up to 1000 nm in dimensions. Alternatively, they may be used which have dimensions of from greater than 1000 nm to 5000 nm. Well-known examples are colloids such as gold colloids and silver colloids. Alternatively, the nanoparticles may be nanoshells such as those taught in U.S. application Ser. Nos. 09/779,677 and 09/038,377, and international application PCT/US00/19268, which are fully incorporated by reference as if expressly disclosed herein. The method typically involves the use of nanoparticles of one composition; however, nanoparticles of more than one composition may be used. If more than one composition of nanoparticles is used, it is typical for the different compositions to all absorb at at least one common wavelength; however, this is not absolutely necessary. As a result, the temporal heating profiles of the different nanoparticles may be the same or different. Typically, the temporal heating profiles are the same. The method may include targeting schemes to direct the nanoparticle to the desired location involving, for example, specific chemical interactions (e.g., antigen-antibody binding, etc.) or may consist of the simple delivery of the therapeutic reagents to the desired area. The direction or targeting of the therapy is primarily for the surface of the subject tissue; however, it may be targeted to other, interior sites. Treatment of the tissue surfaces may be accomplished by non-targeted delivery. Examples of non-targeted delivery include bathing tissue in nanoparticle suspensions, using a pipette or micropipette to apply a nanoparticle suspension to tissue, injecting a nanoparticle suspension into tissue, painting nanoparticles onto tissues, or combining nanoparticles with other ingredients such as one or more polymers and/or one or more proteins or combinations thereof. Examples include, but are not limited to albumin, fibrinogen, collagen, elastin, fibronectin, laminin, chitosan, basic fibroblast growth factor, or vascular endothelial cell growth factor, platelet-derived growth factor, epidermal growth factor, or insulin-like growth factor and directly placing this mixture on or between tissue surfaces. The invention encompasses the use of one or more other chemical entities or moieties to be used in conjunction with the nanoparticles. These species may have a complimentary or additional therapeutic or diagnostic utility. The nanoparticles may be chemically bound to these other components or may be delivered as a simple mixture with them. For example, the nanoparticles may be bound to antibody. The method of repair may involve only one type of nanoparticle or may involve more than one type of nanoparticle. For instance, one type of nanoparticle may be applied to one of the sites to be joined, while another type of nanoparticle may be applied to the other. Alternatively, one or more mixtures of nanoparticles may be applied to one or more of the sites to be joined. Whether the compositions are mixtures of nanoparticles or one type of nanoparticle, they may or may not contain other species, such as one or more types of polymers or one or more types of proteins, or both. It should be noted that the variations outlined above may be used in all the applications of the present invention, from tissue/tissue to tissue/non-tissue to non-tissue/non-tissue application. This is true notwithstanding that some of the specific examples given below may not expressly incorporate some or all of them.

Laser tissue welding refers to techniques by which tissues may be joined in response to exposure to light and the subsequent generation of heat. The goal of these techniques is (i) the rapid joining of tissues with high tensile strength across the union, (ii) union throughout the depth of the targeted tissue, (iii) a minimum of scar tissue formation, and (iv) minimal damage to surrounding tissue. These techniques may also be beneficial in a number of minimally invasive surgical techniques. In the preferred embodiment of the present invention laser excitation sources are used although alternative embodiments utilize non-laser excitation sources. Laser tissue repair is under investigation or in use in many surgical disciplines for procedures such as closure of skin wounds, vascular anastamosis, occular repair, nerve repair, cartilage repair, and liver repair. Currently, laser tissue repair is accomplished either through welding, apposing two tissue surfaces then exposing to laser radiation to heat the tissues sufficiently to join them, or through soldering, wherein an exogenous material such as a protein or synthetic polymer is placed between two tissue surfaces to enhance joining of the tissues upon exposure to laser radiation. The tissue repair and modification techniques described herein are optimally suited to the use of laser light due to the spectral properties (such as the tunability) of the nanoparticles. However, they are also suited for non-laser based excitation. An example of the laser tissue welding embodiment of the present invention is provided below in Example 2.

Ideally, to maximize penetration of light through the depth of the wound and to minimize damage to surrounding tissue, one would prefer to use a laser light source that is not appreciably absorbed by tissues. This can be accomplished using NIR light, specifically in the wavelength region between 600–2000 nm, where penetration of light into tissue is maximal. Exposure to light at these wavelengths will not generate significant heating in tissues, and thus will not induce tissue damage. However, when light at these wavelengths interacts with nanoparticles designed to strongly absorb NIR light, heat will be generated rapidly and sufficiently to induce tissue welding. Because NIR wavelengths of light are highly transmitted through tissue, it is possible to access and treat tissue surfaces that are otherwise difficult or impossible. An example of the capability of the present invention is given below.

Several new classes of such nanoparticles that offer more specific and accurate repair technologies, based on nanoparticles that emit or scatter NIR light and that can be easily conjugated to antibodies, as well as highly localized, targeted, and minimally invasive treatment strategies based on photothermal interactions with nanoparticles, have been developed. In a preferred embodiment to repair targeted tissue, the nanoparticles are nanoshells and are formed with a core of a dielectric or inert material such as silicon, coated with a material such as a highly conductive metal which can be excited using radiation such as NIR light (approximately 750 to 1300 nm). Other nanoparticles absorb across other regions of the electromagnetic spectrum such as the ultraviolet or visible region. Upon excitation, the nanoshells emit heat. The combined diameter of the shell and core of the nanoshells typically ranges from the tens to the hundreds of nanometers. The nanoparticles have dimension of from 1 to 5000 nanometers.

Importantly, in all embodiments of the present invention, the excitation may be effected from an excitation source inside the material to which the tissue repair is to be effected or it may be effected by an excitation source outside the material. In the in vivo applications, it may be effected by an excitation source inside the body or outside the body. In in vivo applications wherein the excitation source is inside the body, the excitation source may be in the subject material or outside it.

NIR light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, such as the use of heated probes, microwaves, ultrasound, lasers, perfusion, radiofrequency energy, and radiant heating is avoided since the levels of radiation used as described herein is insufficient to induce hyperthermia except at the surface of the nanoparticles, where the energy is more effectively concentrated by the metal surface on the dielectric. The currently available methods suffer from the use of generalized as opposed to localized heating or the need for high power radiation sources or both. Targeting molecules can be antibodies or fragments thereof, ligands for specific receptors, or other proteins specifically binding to the surface of the cells to be targeted.

Metal Nanoshells

Metal nanoshells are a type of nanoparticle composed of a dielectric (for instance, silica) core coated with one or more metallic (for instance, gold) layers. The shell layer is formed of a metal or metal-like material that preferably conducts electricity, although materials with sufficiently lower dielectric constants than the core material can also be used. Preferred metals include gold, silver, copper, platinum, palladium, lead, nickel and iron. Gold is most preferred. Gold nanoshells possess physical properties similar to gold colloid, in particular, a strong optical absorption due to the collective electronic response of the metal to light. The optical absorption of gold colloid yields a brilliant red color which has been of considerable utility in consumer-related medical products, such as home pregnancy tests. In contrast, the optical response of gold nanoshells depends dramatically on the relative size of the nanoparticle core and the thickness of the gold shell (Neeves & Bimboim, 1989; Kreibig and Vollmer, 1995). By varying the relative core and shell thicknesses, the color of gold nanoshells can be varied across a broad range of the optical spectrum that spans the visible and the NIR spectral regions.

Gold nanoshells can be made to either preferentially absorb or scatter light by varying the size of the particle relative to the wavelength of the light at their optical resonance. Other materials may also be used. Organic conducting materials such as polyacetylene and doped polyanaline can also be used. Additional layers, such as a non-conducting layer, a conducting layer, or a sequence of such layers, such as an alternating sequence of conducting and non-conducting layers, can be bound to the shell layer. The core should be non-conducting, for example, formed of a dielectric material or semiconductor material. Examples include silicon dioxide, titanium dioxide, polymethyl methacrylate (PMMA), polystyrene, gold sulfide, and macromolecules such as dendrimers. Exemplary semiconductive materials include CdSe, CdS, and GaAs. The nature of the material affects the properties of the particles. For example, if the dielectric constant of the shell layer is larger relative to a particle having a core with a given dielectric constant, the absorbance maximum of the particle will be blue-shifted relative to a particle having a core with a lower dielectric constant. The preferred core material is colloidal silica, which can be prepared by base catalyzed reaction of tetraalkoxysilanes. The shell layer and core can be linked, for example, through ionic bonds, lone-pair interactions, hydrogen bonds, or Van der Waals interaction. An exemplary linker is aminopropyltriethoxysilane.

In the typical embodiment, the nanoshells are not biodegradable but will tend to be cleared following administration by the reticuloendothelial system (RES). However, in some embodiments, it may be desirable to link the core, the metal shell or an intervening layer, using biodegradable materials such as a polyhydroxy acid polymer which degrades hydrolytically in the body so that removal of the particles after a period of time is facilitated.

In the preferred embodiment, the nanoshells are homogeneous in size distribution and shape. Although described herein with reference to spherical particles, other shapes can be fabricated using the same methods. Examples are irregular particles, cylinders, disks, and other geometric shapes. Typically, the thickness of the shell will be between one and thirty nanometers. However, cores can range from 10 nm to greater than four microns and shell layers can range from one to 100 nm in thickness.

A comprehensive investigation of the optical properties of metal nanoshells is reported by Averitt et al., 1997, as well as Averitt, et al., 1999. Quantitative agreement between Mie scattering theory and the experimentally observed optical resonant properties has been achieved. Based on this success, it is now possible to predictively design gold nanoshells with the desired optical resonant properties, and then to fabricate the nanoshell with the dimensions and nanoscale tolerances necessary to achieve these properties (Oldenburg, et al., 1998).

Production of Antibodies

The term antibody is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides antibodies of the human, murine, monkey, rat, hamster, rabbit and chicken origin.

However, humanized antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

Antibodies may be further purified, if desired, using filtration, centrifugation and various chromatographic methods such as HPLC or affinity chromatography. Fragments of the antibodies of the invention can be obtained from the antibodies so produced by methods which include digestion with enzymes such as pepsin or papain, and/or by cleavage of disulfide bonds by chemical reduction. Alternatively, antibody fragments encompassed by the present invention can be synthesized using an automated peptide synthesizer or by expression of full-length gene or gene fragments in $E.$ $coli.$ It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Nanoparticle Conjugated Antibodies

Because the metal layer of gold nanoshells is grown using the same chemical reaction as gold colloid synthesis, the surfaces of gold nanoshells are virtually chemically identical to the surfaces of the gold nanoparticles universally used in bioconjugate applications. The use of gold colloid in biological applications began in 1971, when Faulk and Taylor invented immunogold staining.

These particles may be subsequently aminated via reaction with aminopropyltriethoxysilane, thus allowing several options for antibody conjugation. Antibodies can be covalently immobilized to either hydroxylated or aminated nanoparticle surfaces via a variety of chemical schemes, including carbodiimide chemistry, diisocyanate linkers, succinimidyl esters, etc. In addition, antibodies can be immobilized via polymer tethering chains. This can be accomplished with difunctional polyethylene glycol derivatives. This immobilization scheme may increase the biological activity of the immobilized antibodies by enhancing their mobility and thus their ability to interact with their target ligand. Efficiency of antibody immobilization can be determined with horseradish peroxidase (HRP) labeled antibodies. Activity of the nanoparticle-conjugated antibodies can be assessed with HRP labeled antigens and by examining nanoparticle binding to antigen-coated surfaces. Nanoparticle binding to these surfaces can be quantitatively assessed by atomic force microscopy (AFM) and fluorescence. Results can be compared to ELISA measurements of the antigen surface concentration.

Other Nanoparticle Systems

Other chemical or biochemical species may be used with nanoparticles in a mixed system to modify or otherwise enhance their properties for the specific application. For instance, they may be in a composition also containing proteins, polymers, or other chemical entities or moieties that aid in the delivery to the desired location. Mixtures of other components may be used with nanoparticles. They may be mixed or bound to antigens to take advantage of the specificity of immunochemical binding. In addition to simple mixtures, these other species may be chemically bound as moieties to the nanoparticles.

The following examples further describe the applications of nanoparticle-based tissue welding. They are merely illustrated and not exhaustive.

EXAMPLE 1

Preparation and Photophysical Properties of Metal Nanoshells

The synthetic protocol for the fabrication of gold nanoshells is based on the well-known principles of molecular self-assembly and colloid chemistry in aqueous solution. The method is straightforward in concept:

1. Grow or obtain silica nanoparticles dispersed in solution, for example, the silicon dioxide particles such as LUDOX TM-50 colloidal silica particles available from Aldrich Chemical Co., Milwaukee, Wis.

2. Attach very small (1–2 nm) metal "seed" colloid to the surface of the nanoparticles via molecular linkages; these seed colloids cover the dielectric nanoparticle surfaces with a discontinuous metal colloid layer, 3. Grow additional metal onto the "seed" metal colloid adsorbates via chemical reduction in solution.

Tethered clusters of metals, ions or atoms are linked to the core particle through a linker molecule. In general, metal is deposited onto the tethered clusters until a coherent metal shell of the desired thickness is formed. This may be by reduction of solution metal or by a colloid-based deposition process. Deposition can be initiated or driven photochemically. This approach has been used to grow both gold and silver metallic shells onto silica nanoparticles.

For any given particle, the maximum absorbance depends upon the ratio of the thickness of the non-conducting layer to the conducting shell layer. The spectral location of the maximum of the plasmon resonance peak depends upon the ratio of the core radius to shell thickness, as well as the dielectric functions of the core and shell. The presence of a dielectric core shifts the plasmon resonance to longer wavelengths relative to a solid nanoparticle made exclusively of the metallic shell material. For a given core radius, a thin shell will have a plasmon peak that is shifted to longer wavelengths relative to a thicker shell. Metal nanoshells offer resonance tunability that solid nanoparticles lack.

Based on the core/shell ratios that can be achieved with this protocol, gold nanoshells with optical resonances extending from the visible region to approximately 3 microns in the infrared can be fabricated. This spectral region includes the 800–1300 nm and 1600–1850 nm "water windows" of the NIR, a region of high physiological transmissivity.

The optical properties of gold nanoshells, when coupled with their biocompatibility and their ease of bioconjugation, render these nanoparticles ideal for the laser welding applications of the present invention.

EXAMPLE 2

Gold-Silica Nanoshells to Enhance Laser Tissue Welding Methods

Gold-Silica nanoshells were prepared as previously described in copending application Ser. No. 09/779,677, with an absorption maximum at approximately 850 nm as shown in FIG. 1. The edges of two pieces of tissue (chicken muscle) were coated with an aqueous suspension of these nanoshells, then positioned such that the two nanoshell-treated surfaces were in contact with one another. In the control case, two pieces of tissue were positioned similarly, but without nanoshell treatment. The tissues were then exposed to light from a diode laser (821 nm, 2.5 W/cm$^2$) for 2 minutes. After exposure to light, tissues were examined for union between the two pieces.

Results

Figure 2:
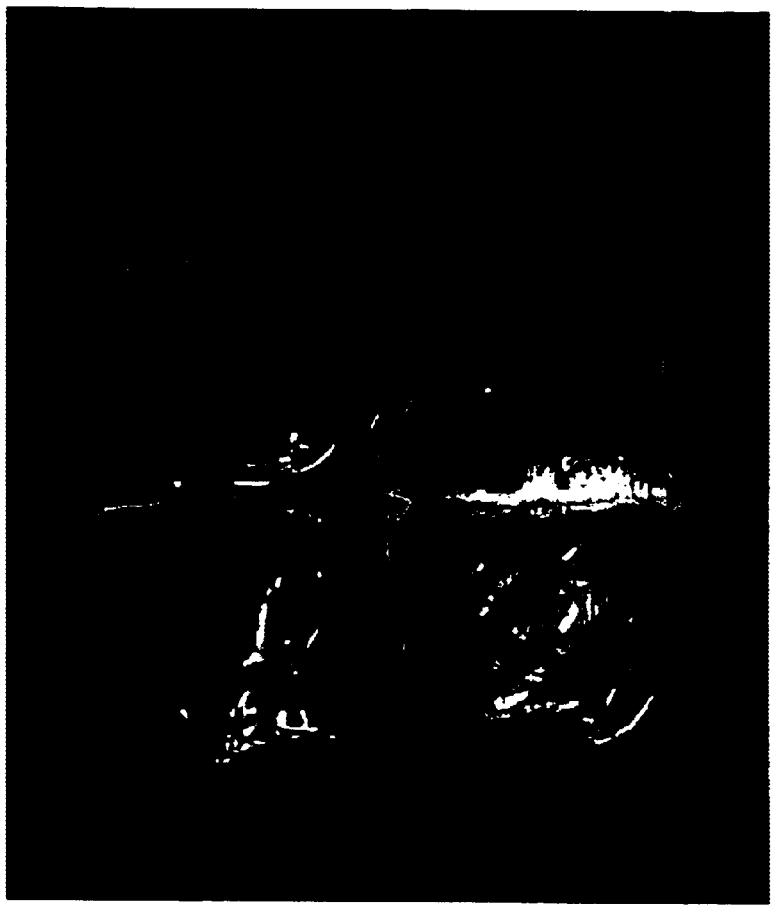
FIG. 2 illustrates two pieces of tissue (chicken muscle) joined by the nanoshell/laser treatment of Example 3; Top sample, Control without nanoshells; Bottom sample with nanoshells.
Figure 3:
FIG. 3 demonstrates the integrity of the union between two pieces of chicken muscle tissue formed by the treatment of Example 3.

As shown in the lower panel of FIG. 2 and in FIG. 3, the muscle samples were effectively joined after exposure to laser radiation only when they were treated with the nanoshell suspension. Without nanoshell treatment, the two pieces of tissue remained entirely separate with no evidence of union between them (upper panel, FIG. 2).

EXAMPLE 3

Cartilage Replacement or Repair

A flap of tissue (like cartilage) is welded to base tissue from which it is torn or as a replacement to lost tissue. The nanoshells are painted on the back of the surface and the laser light passed through the flap to join the base to the flap with minimum damage to the flap. It is also applicable where the light source is outside the body or there is other intervening tissue between the surfaces to be welded and the light source. For instance, a cartilage repair with the laser source outside the body.

EXAMPLE 4

Arterial Repair

In joining an artery or other structure where the weld must go around the tissue, use of IR and nanoshells is used to direct the beam through the tissue and achieve a weld on all sides, and through the thickness of the structure without rotation of the laser light source.

EXAMPLE 5

Induction of Coagulation

Additionally, absorbing nanoparticles are used to induce coagulation. For example, the bleeding surface is sprayed with a nanoparticles suspension then exposed to an appropriate light source. Coagulation is induced at the surface due to the heat generated by the nanoparticles. Damage to the tissue is localized to close to the tissue surface, whereas more conventional techniques, such as electrocautery, induce more widespread tissue damage. Such techniques to induce coagulation are useful in surgical and non-surgical applications.

EXAMPLE 6

Heat-Induced Modification of Tissues

This invention is also useful for heat-induced modification of tissues or proteins. Conventional laser resurfacing is a technique used for removal and/or minimization of wrinkles and involves the direct application of laser light to the tissue to be treated. Laser light is applied to the skin and as a result of heating, collagen and elastin fibers in the dermis are reorganized. Such laser treatments, often referred to as laser resurfacing, have been found to be effective for the reduction of wrinkles in the skin, presumably through the generation of heat within the tissue. Reduction in wrinkles has been attributed to the remodeling of matrix proteins, including the stimulation of collagen and elastin synthesis and the contracture of collagen fibrils (Fitzpatrick, et al., 2000; Goldberg, et al., 2000; Bjerring, et al., 2000). However, a major drawback of laser resurfacing techniques has been the extensive damage to the epidermal tissue. This occurs because the absorption of light in these systems is targeted for normal tissue components or water, and thus, heat is generated throughout the tissue. Cryogen spray cooling techniques, wherein the surface of the epidermis is cooled before exposure to the laser so that the final temperature reached in the epidermis will be lower than in the dermis, have been investigated to combat this problem.

Nanoparticles can be targeted, either mechanically or chemically to a specific region of the tissue in order to localize light absorption, and thus heating, to the desired area. In wrinkle reduction, nanoparticles are targeted to the dermis to initiate matrix remodeling while minimizing damage to the epidermis. The highly controlled heating of tissue of is accomplished by targeting nanoparticles to a specific depth or region of tissue to more strictly localize heating and more effectively avoid damage to "non-targeted" tissue. In the case of skin and wrinkle reduction, it is possible to target nanoparticles to "sub-epidermis" tissue using ballistic devices similar to the so-called "Gene Gun" or using tattoo needles.

EXAMPLE 7

Joining Tissue with Non-Tissue Material or Non-Tissue Material with Non-Tissue Material The instant invention is also useful for the joining of tissue to non-tissue material such as a medical device or engineered tissue. The invention is also useful in non-biological contexts, such as the joining of two polymer materials such as, for example, polyethylene and/or polypropylene. Welding of plastics has been demonstrated (Chipperfield, 2001). Because of the ability to deliver localized, highly controlled heating, the technique is useful for the microfabrication of devices, both biological and non-biological. This high degree of temperature and location control affords the ability to effect a nearly seamless union. The invention is useful in welding of non-tissue materials in a non-biological context, such as the joining of two fissured polymer materials such as polyethylene. In the case of tissue/non-tissue applications, the nanoparticles are delivered directly to the tissue or impregnated into or coated onto the non-tissue material. Alternatively, they are incorporated into the both the tissue and non-tissue material. In another application, the method is used to join two polymeric or protein-based materials. One or both of the materials to be joined may be non-tissue material. For example, the welding of two medical devices may be desirable. As in other applications, the nanoparticles may be delivered to one or both of the two materials to be joined. In the case of welding of tissue to non-tissue, the nanoparticles may be applied to the tissue or to both the tissue and the non-tissue material. The denaturation of proteins and other materials in the tissue should allow for adhesion of the tissue to most materials. In the case of the welding non-tissue materials, one of skill in the art will recognize that the judicious choice of nanoparticles will be useful in optimizing the results. The thermal properties of one or more of the materials to be welded should be considered. For instance, materials having a relatively high melting point will require nanoparticles that have thermal profiles characterized by a rapid rise in temperature and a significant release of heat. In such cases, a higher concentration of nanoparticles and a higher power level of the excitation source will be used. In the case of medical devices, the most likely scenario is the need to fuse materials such as polyethylene; relatively mild conditions of nanoparticle temperature and laser power should be adequate to weld this material in most cases. One of skill in the art in reading the specification would immediately recognize the parameters that should be optimized to effect a weld between two non-tissue materials.

EXAMPLE 8

Joining Tissue with Soldering Material

Nanoshells were suspended in a viscous solder media composed of 20–50% (w/v) bovine serum albumin (BSA). In this highly-viscous media, the nanoshells were placed directly on the surface to be welded with no apparent migration. These concentrated aqueous nanoshell solders exhibited an attenuation coefficient of approximately 300 $cm^{-1}$ at 830 nm. A preliminary protocol was developed for use with fresh chicken tendons or shaved rat skin. After a small tendon or other piece of tissue was cut in half, a small amount of solder was applied on the surfaces to be reconnected. Only a small amount of solder was required, for example, 5 $\mu$L per cm of cut was appropriate for rat skin. Various methods for deposition were investigated, including the use of a pipette and a cannula. The pieces of tissues were lined back up to their pre-cut orientation. A quick pass with the laser (5 sec/cm) on the solder seam served to make a preliminary bond. Then two long laser passes (15 sec/cm) were made at a 45° angle (relative to the first seam) aimed to penetrate to deeper solder locations and strengthen the bond. Welds of rat skin and chicken tendons made with this procedure were complete and had significant tensile strength when assessed qualitatively.

EXAMPLE 9

Tissue Ablation

This invention is also useful for tissue ablation by increasing the power of the light source used. This tissue ablation embodiment is easily adapted for use in laparascopic, arthroscopic, or catheter-based devices.

The invention is also applicable to non-human and non-biological systems (such as polymers) where use of a strong absorber can enhance the ability to create a weld with minimal damage to the joined or surrounding material. This facilitates access to otherwise hidden or difficult to access areas, particularly where the materials are transparent or are optically less absorbing to the wavelength that the nanoshells are tuned to absorb.

The invention is also applicable for use in conjunction with convention tissue joining techniques such as simple suturing of tissue. The use of nanoparticle-based welding will enhance the healing process and potentially help minimize scarring.

The foregoing is intended to demonstrate specific embodiments of the invention. The teachings, disclosures, and examples are merely illustrative and not exhaustive of the applications of the present invention. One of skill in the art readily appreciates that the present invention is well adapted to carry out the objectives and obtain the ends and advantages mentioned as well as those inherent therein. Changes therein and other uses will occur to those skilled in the art which are encompassed within the spirit of the invention or defined by the scope of the pending claims. It should be appreciated by those of skill in the art that the techniques disclosed represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

REFERENCES CITED

All patents and publications mentioned in the specification are indicative of the level of those skilled in the art to which the invention pertains. All patents and publications are herein incorporated by reference to the same extent as if each individual publication was specifically and individually indicated to be incorporated by reference.

Fried et al. U.S. Pat. No. 6,221,068 (2001)

U.S. application Ser. No. 09/038,377

U.S. application Ser. No. 09/779,677

R. D. Averitt; Plasmon Resonance Shifts of Au-Coated $Au_2S$ Nanoshells: Insight into Multicomponent Nanoparticle Growth, Am. Phys. Soc., Jun. 2, 1997, 78:22, 4217–4220.

S. J. Oldenburg, et al.; *Nanoengineering of Optical Resonances*, Chemical Physics Letters, 1998, 288, 243–347.

J. F. Birch, D. J. Mandley, S. L. Williams, D. R. Worrall, P. J. Trotter, F. Wilkinson, P. R. Bell; *Lasers in Surgery and Medicine*, 26:323–9 (2000).

C. S. Cooper, I. P. Schwartz, D. Suh, A. J. Kirsch; *Lasers in Surgery and Medicine*, 29:53–61 (2000).

C. S. Cooper, I. P. Schwartz, D. Suh, A. J. Kirsch: Optimal solder and power density for diode laser tissue soldering (LTS), Lasers Surg. Med. Vol. 29, 2001:53–61.

K. M. McNally, B. S. Sorg, A. J. Welch; *Lasers in Surgery and Medicine*, 27:147–57 (2000).

K. M. McNally, B. S. Sorg, A. J. Welch, J. M. Dawes, E. R. Owen; Novel solid protein solder designs for laser-assisted tissue repair. Lasers Surg Med. Vol. 27, 2000:147–57.

K. M. McNally, B. S. Sorg, A. J. Welch, J. M. Dawes, E. R. Owen,; Photothermal effects of laser tissue soldering, Phys Med Biol. Vol. 44, 1999:983–1002; discussion 2 pages follow.

B. S. Sorg, K. M. McNally, A. J. Welch; *Lasers in Surgery and Medicine*, 27:73–81 (2000).

B. S. Sorg, A. J. Welch; *Lasers in Surgery and Medicine*, 28:297–306 (2001).

K. M. McNally, B. S. Sorg, A. J. Welch; *Lasers in Surgery and Medicine*, 27:147–57 (2000).

K. M. McNally, B. S. Sorg, E. K. Chan, E. J. Welch, J. M. Dawes, E. R. Owen; *Lasers in Surgery and Medicine*, 26:346–56 (2000).

B. Lobel, O. Eyal, N. Kariv, A. Katzir; *Lasers in Surgery and Medicine*, 26:4–12 (2000).

N. M. Fried, B. Choi, A. J. Welch, J. T. Walsh; *Lasers in Surgery and Medicine*, 25:291–303 (1999).

N. M. Fried, J. T. Walsh, Jr.; Laser skin welding: in vivo tensile strength and wound healing results. Lasers Surg Med. Vol. 27, 200:55–65.

F. A. Chipperfield, I. A. Jones; Medical Device Technology, 12:40–4 (2001).

R. E. Fitzpatrick, E. F. Rostan, N. Marchell; *Lasers in Surgery and Medicine*, 27:395–403 (2000).

D. J. Goldberg; *Journal of Cutaneous Laser Therapy*, 2:59–61 (2000)

P. Bjerring, M. Clement, L. Heickendorff, H. Egevist, M. Kiernan; *Journal of Cutaneous Laser Therapy*, 2:9–15 (2000).

Welch A J, van Gemert M J C. Optical-Thermal Response of Laser Irradiated Tissue. In: van Gemert M J C, ed. New York: Plenum Press, 1995.

Duck F A. Physical Properties of Tissue: A Comprehensive Reference Book. San Diego: Academic Press, 1990.

Anderson R R, Vollmer M. The Optics of Human Skin. J Invest Dermatol. Vol. 77, 1981:13–19.

Bass L S, Treat M R. Laser tissue welding: a comprehensive review of current and future clinical applications. Lasers Surg Med. Vol. 17, 1995:315–49.

Reiss S M. Laser Tissue Welding: The Leap from the Lab to the Clinical Setting. Biophotonics International, 2001:36–40.

Capon A, Souil E, Gauthier B, et al. Laser assisted skin closure (LASC) by using a 815-nm diode-laser system accelerates and improves wound healing. Lasers Surg Med. Vol. 28, 2001:168–75.

Kirsch A J, Duckett J W, Snyder H M, et al. Skin flap closure by dermal laser soldering: a wound healing model for sutureless hypospadias repair. Urology. Vol. 50, 1997:263–72.

Simhon D, Ravid A, Halpern M, et al. Laser soldering of rat skin, using fiberoptic temperature controlled system. Lasers Surg Med. Vol. 29, 2001:265–73.

Wider T M, Libutti S K, Greenwald D P, et al. Skin closure with dye-enhanced laser welding and fibrinogen. Plast Reconstr Surg. Vol. 88, 1991:1018–25.

DeCoste S D, Farinelli W, Flotte T, Anderson R R. Dye-enhanced laser welding for skin closure. Lasers Surg Med. Vol. 12, 1992:25–32.

Fung L C, Mingin G C, Massicotte M, Felsen D, Poppas D P. Effects of temperature on tissue thermal injury and wound strength after photothermal wound closure. Lasers Surg Med. Vol. 25, 1999:285–90.

Massicotte J M, Stewart R B, Poppas D P. Effects of endogenous absorption in human albumin solder for acute laser wound closure. Lasers Surg Med. Vol. 23, 1998:18–24.

Godlewski G, Rouy S, Tang J, Dauzat M, Chambettaz F, Salathe R P. Scanning electron microscopy of microarterial anastomoses with a diode laser: comparison with conventional manual suture. J Reconstr Microsurg. Vol. 11, 1995:37–41; discussion 42.

Lauto A, Hamawy A H, Phillips A B, et al. Carotid artery anastomosis with albumin solder and near infrared lasers: a comparative study. Lasers Surg Med. Vol. 28, 2001:50–5.

Murray L W, Su L, Kopchok G E, White R A. Crosslinking of extracellular matrix proteins: a preliminary report on a possible mechanism of argon laser welding. Lasers Surg Med. Vol. 9, 1989:490–6.

Ott B, Zuger B J, Erni D, et al. Comparative in vitro study of tissue welding using a 808 nm diode laser and a Ho:YAG laser. Lasers Med Sci. Vol. 16, 2001:260–6.

Chuck R S, Oz M C, Delohery T M, et al. Dye-enhanced laser tissue welding. Lasers Surg Med. Vol. 9, 1989:471–7.

Kirsch A J, de Vries G M, Chang D T, Olsson C A, Connor J P, Hensle T W. Hypospadias repair by laser tissue soldering: intraoperative results and follow-up in 30 children. Urology. Vol. 48, 1996:616–23.

Maragh H, Hawn R S, Gould J D, Terzis J K. Is laser nerve repair comparable to microsuture coaptation? J Reconstr Microsurg. Vol. 4, 1988:189–95.

Lauto A, Trickett R, Malik R, Dawes J M, Owen E R. Laser-activated solid protein bands for peripheral nerve repair: an vivo study. Lasers Surg Med. Vol. 21, 1997:134–41.

Menovsky T, Beek J F. Laser, fibrin glue, or suture repair of peripheral nerves: a comparative functional, histological, and morphometric study in the rat sciatic nerve. J Neurosurg. Vol. 95, 2001:694–9.

Bleustein C B, Sennett M, Kung R T, Felsen D, Poppas D P, Stewart R B. Differential scanning calorimetry of albumin solders: interspecies differences and fatty acid binding effects on protein denaturation. Lasers Surg Med. Vol. 27, 2000:465–70.

Cilesiz I, Springer T, Thomsen S, Welch A J. Controlled temperature tissue fusion: argon laser welding of canine intestine in vitro. Lasers Surg Med. Vol. 18, 1996:325–34.

Lauto A, Stewart R, Ohebshalom M, Nikkoi N D, Felsen D, Poppas D P. Impact of solubility on laser tissue-welding with albumin solid solders. Lasers Surg Med. Vol. 28, 2001:44–9.

Zuger B J, Ott B, Mainil-Varlet P, et al. Laser solder welding of articular cartilage: tensile strength and chondrocyte viability. Lasers Surg Med. Vol. 28, 2001:427–34.

Wadia Y, Xie H, Kajitani M. Liver repair and hemorrhage control by using laser soldering of liquid albumin in a porcine model. Lasers Surg Med. Vol. 27, 2000:319–28.

Guthrie C R, Murray L W, Kopchok G E, Rosenbaum D, White R A. Biochemical mechanisms of laser vascular tissue fusion. J Invest Surg. Vol. 4, 1991:3–12.

Robinson J K, Garden P M, Taute P M, Leibovich S J, Lautenschlager E P, Hartz R S. Wound Healing in Porcine Skin Following Low-Output Carbon Dioxside Laser Irradiation of the Incision. Ann Plast Surg. Vol. 18, 1987:499–505.

Bass L S, Moazami N, Pocsidio J, Oz M C, LoGerfo P, Treat M R. Changes in type I collagen following laser welding. Lasers Surg Med. Vol. 12, 1992:500–5.

Bleustein C B, Felsen D, Poppas D P. Welding characteristics of different albumin species with and without fatty acids. Lasers Surg Med. Vol. 27, 2000:82–6.

Poppas D P, Choma T J, Rooke C T, Klioze S D, Schlossberg S M. Preparation of human albumin solder for laser tissue welding. Lasers Surg Med. Vol. 13, 1993:577–80.

Kirsch A J, Canning D A, Zderic S A, Hensle T W, Duckett J W. Laser Soldering Technique for Sutureless Urethral Surgery. Techniques in Urology. Vol. 3, 1997:108–113.

Ott B, Zueger B J, Koestli K, et al. Dye-Enchanced Laser Soldering of Cartilage and Blood Vessels. Laser Physics. Vol. 12, 2002:635–640.

Small I V W, Heredia N J, Maitland D J, Da Silva L B, Matthews D L. Dye-Enhanced Protein Solders and Patches in Laser-Assisted Tissue Welding. J Clin Laser Med Surg. Vol. 15, 1997:205–208.

Bleustein C B, Walker C N, Felsen D, Poppas D P. Semi-solid albumin solder improved mechanical properties for laser tissue welding. Lasers Surg Med. Vol. 27, 2000:140–6.

Lauto A, Ohebshalom M, Esposito M, et al. Self-expandable chitosan stent: design and preparation. Biomaterials 2001; 22:1869–74.

Cilesiz I. Controlled Temperature Photothermal Tissue Welding. Journal of Biomedical Optics. Vol. 4, 1999:327–336.

We claim:

1. A method of joining tissue comprising the steps of:
   delivering nanoparticles having dimensions of from 1 to 1000 nanometers that absorb light at one or more wavelengths to the tissue to be joined; and,
   exposing said nanoparticles to light at one or more wavelengths that are absorbed by the nanoparticles.

2. The method of claim 1, wherein said light is laser light.

3. The method of claim 1, wherein said nanoparticles absorb said light and convert said light to heat.

4. The method of claim 1, wherein said nanoparticles are nanoshells.

5. The method of claim 4, wherein said nanoshells are metal nanoshells.

6. The method of claim 5, where said metal nanoshells absorb IR light and generate heat.

7. The method of claim 4, wherein said nanoshells absorb a particular wavelength and generate heat.

8. The method of claim 1, wherein said nanoparticles are metal colloids.

9. The method of claim 8, wherein said metal colloids are selected from the group consisting of gold colloids and silver colloids.

10. The method of claim 1, wherein said nanoparticles are fullerenes.

11. The method of claim 1, wherein said nanoparticles are all of the same composition.

12. The method of claim 1, wherein said light is selected from the group consisting of ultraviolet, visible, infrared and a combination thereof.

13. The method of claim 1, wherein at least a portion of said nanoparticles is mixed with one or more proteins.

14. The method of claim 13, wherein said one or more proteins is selected from the group consisting of albumin, fibrinogen, collagen, elastin, fibronectin, laminin, chitosan, fibroblast growth factor, vascular endothelial cell growth factor, platelet-derived growth factor, epidermal growth factor, or insulin-like growth factor and combinations thereof.

15. The method of claim 1, wherein at least a portion of said nanoparticles is mixed with one or more polymers.

16. The method of claim 15, wherein said one or more polymers is selected from the group consisting of polyethylene, polyethylene glycol, polystyrene, polyethylene terephthalate, polymethyl methacrylate and combinations thereof.

17. The method of claim 1, wherein at least a portion of said nanoparticles are mixed with one or more polymers and one or more proteins.

18. The method of claim 1, wherein at least a portion of said nanoparticles is bound to a chemical moiety.

19. The method of claim 1, wherein at least a portion of said nanoparticles is bound to an antibody.

20. The method of claim 1, wherein said light is within the range of 600–2000 nm.

21. The method of claim 1, wherein said wavelength of light is within the range of 700–1200 nm.

22. The method of claim 1, wherein said wavelength of light is within the range of 750–1100 nm.

23. A method of joining tissue comprising the steps of:
   delivering nanoparticles having dimensions of from greater than 1000 to 5000 nanometers that absorb light at one or more wavelengths to the tissue to be joined; and,
   exposing said nanoparticles to light at one or more wavelengths that are absorbed by the nanoparticles.

24. The method of claim 23, wherein said light is laser light.

25. The method of claim 23, wherein said nanoparticles absorb said light and convert said light to heat.

26. The method of claim 23, wherein said nanoparticles are nanoshells.

27. The method of claim 26, wherein said nanoshells are metal nanoshells.

28. The method of claim 27, where said metal nanoshells absorb IR light and generate heat.

29. The method of claim 26, wherein said nanoshells absorb a particular wavelength and generate heat.

30. The method of claim 23, wherein said nanoparticles are metal colloids.

31. The method of claim 30, wherein said metal colloids are selected from the group consisting of gold colloids and silver colloids.

32. The method of claim 23, wherein said nanoparticles are fullerenes.

33. The method of claim 23, wherein said nanoparticles are all of the same composition.

34. The method of claim 23, wherein said light is selected from the group consisting of ultraviolet, visible, infrared and a combination thereof.

35. The method of claim 23, wherein at least a portion of said nanoparticles is mixed with one or more proteins.

36. The method of claim 35, wherein said one or more proteins is selected from the group consisting of albumin, fibrinogen, collagen, elastin, fibronectin, laminin, chitosan, fibroblast growth factor, vascular endothelial cell growth factor, platelet-derived growth factor, epidermal growth factor, or insulin-like growth factor and combinations thereof.

37. The method of claim 23, wherein at least a portion of said nanoparticles is mixed with one or more polymers.

38. The method of claim 37, wherein said one or more polymers is selected from the group consisting of polyethylene, polyethylene glycol, polystyrene, polyethylene terephthalate, polymethyl methacrylate and combinations thereof.

39. The method of claim 23, wherein at least a portion of said nanoparticles are mixed with one or more polymers and one or more proteins.

40. The method of claim 23, wherein at least a portion of said nanoparticles is bound to a chemical moiety.

41. The method of claim 23, wherein at least a portion of said nanoparticles is bound to an antibody.

42. The method of claim 23, wherein said light is within the range of 600–2000 nm.

43. The method of claim 23, wherein said wavelength of light is within the range of 700–1200 nm.

44. The method of claim 23, wherein said wavelength of light is within the range of 750–1100 nm.

45. The method of claim 23 wherein said nanoparticles have dimensions of from 2000 nm to 5000 nm.

46. A method of joining tissue to non-tissue material comprising the steps of:
    delivering a first set of nanoparticles that absorb light at one or more wavelengths to the tissue to be joined; and
    delivering a second set of nanoparticles that absorb light at one or more wavelengths to the non-tissue material; and
    exposing the first set of said nanoparticles and the second set of nanoparticles to light at one or more wavelengths that are absorbed by the first set of nanoparticles and the second set of nanoparticles.

47. The method of claim 46, wherein the first set of nanoparticles and the second set of nanoparticles are the same.

48. The method of claim 46, wherein the first set of nanoparticles and the second set of nanoparticles are different.

49. The method of claim 46, wherein the first set of nanoparticles and the second set of nanoparticles are mixed with a protein, polymer or combination thereof.

50. The method of claim 46, wherein the first set of nanoparticles are mixed with a protein, polymer or combination thereof.

51. The method of claim 46, wherein the second set of nanoparticles are mixed with a protein, polymer or a combination thereof.

52. The method of claim 46, wherein the first and second sets of nanoparticles absorb light at at least one common wavelength.

53. The method of claim 46, wherein said step of exposing results in different heating profiles for the sets of nanoparticles.

54. The method of claim 46, wherein said light is laser light.

55. The method of claim 46, wherein said non-tissue comprises a medical device.

56. The method of claim 46, wherein said non-tissue comprises engineered tissue.

57. A method for reducing wrinkles in tissue comprising the steps of:
    delivering nanoparticles that absorb light at one or more wavelengths to the tissue; and
    exposing said nanoparticles to light at one or more wavelengths that are absorbed by the nanoparticles.

58. A method for resurfacing tissue comprising the steps of:
    delivering nanoparticles that absorb light at one or more wavelengths to the tissue; and
    exposing said nanoparticles to light at one or more wavelengths that are absorbed by the nanoparticles.

59. A method of ablating tissue comprising the steps of:
    delivering nanoparticles that absorb light at one or more wavelengths to the tissue; and,
    exposing said nanoparticles to light at one or more wavelengths that are absorbed by the nanoparticles.

60. A method of inducing coagulation of blood comprising the steps of:
    delivering nanoparticles that absorb light at one or more wavelengths to tissue; and,
    exposing said nanoparticles to light at one or more wavelengths that are absorbed by the nanoparticles.

61. A method of joining non-tissue materials comprising the steps of:
    delivering nanoparticles that absorb light at one or more wavelengths to one or more of the materials; and,
    exposing said nanoparticles to light at one or more wavelengths that are absorbed by the nanoparticles.

62. A method of joining tissue comprising the steps of:
    delivering nanoshells to the tissue, said nanoshells having a light wavelength extinction maximum between 750 and 1100 nanometers; and,
    exposing said nanoshells to light at wavelengths between 750 and 1100 nanometers.

63. The method of claim 62, wherein at least a portion of said nanoshells is mixed with one or more proteins.

64. The method of claim 63, wherein said one or more proteins is selected from the group consisting of albumin, fibrinogen, collagen, elastin, fibronectin, laminin, chitosan, fibroblast growth factor, vascular endothelial cell growth factor, platelet-derived growth factor, epidermal growth factor, or insulin-like growth factor and combinations thereof.

* * * * *

US006685730C1

(12) EX PARTE REEXAMINATION CERTIFICATE (11747th)
United States Patent
West et al.

(10) Number: US 6,685,730 C1
(45) Certificate Issued: Oct. 30, 2020

(54) OPTICALLY-ABSORBING NANOPARTICLES FOR ENHANCED TISSUE REPAIR

(75) Inventors: Jennifer L. West, Pearland, TX (US); Rebekah Drezek, Houston, TX (US); Scott Sershen, San Francisco, CA (US); Nancy J. Halas, Houston, TX (US)

(73) Assignee: RICE UNIVERSITY, Houston, TX (US)

Reexamination Request:
No. 90/013,883, Dec. 21, 2016

Reexamination Certificate for:
Patent No.: 6,685,730
Issued: Feb. 3, 2004
Appl. No.: 10/254,233
Filed: Sep. 25, 2002

Related U.S. Application Data

(60) Provisional application No. 60/325,038, filed on Sep. 26, 2001.

(51) Int. Cl.
*A61N 5/06* (2006.01)
*A61N 5/067* (2006.01)
*A61K 47/69* (2017.01)
*A61K 41/00* (2020.01)
*A61L 24/00* (2006.01)
*A61L 26/00* (2006.01)
*A61B 18/20* (2006.01)

(52) U.S. Cl.
CPC ............. *A61N 5/06* (2013.01); *A61B 18/20* (2013.01); *A61K 41/008* (2013.01); *A61K 47/6929* (2017.08); *A61L 24/0089* (2013.01); *A61L 26/0004* (2013.01)

(58) Field of Classification Search
None
See application file for complete search history.

(56) References Cited

To view the complete listing of prior art documents cited during the proceeding for Reexamination Control Number 90/013,883, please refer to the USPTO's public Patent Application Information Retrieval (PAIR) system under the Display References tab.

*Primary Examiner* — Glenn K Dawson

(57) ABSTRACT

This invention is generally in the field of improved methods for the localized delivery of heat and the use thereof for the repair of tissue. The method involves localized induction of hyperthermia in tissue or materials by delivering nanoparticles to the tissue or materials and exposing the nanoparticles to an excitation source under conditions wherein they emit heat. The generation of heat effects the joining of the tissue or materials.

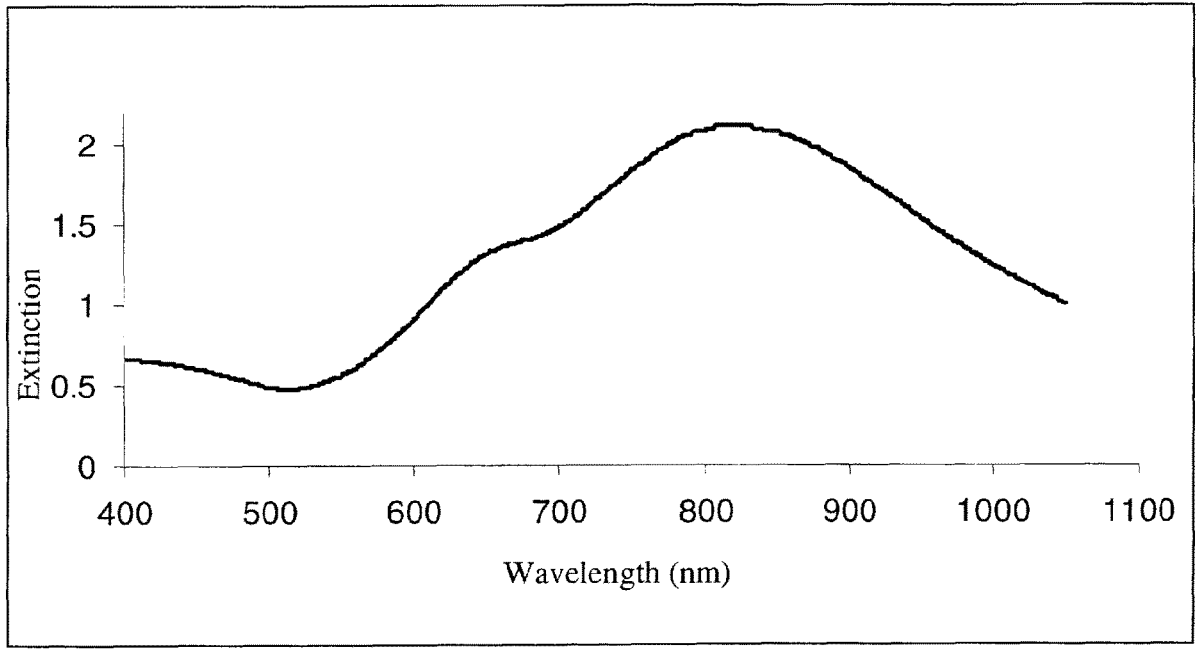

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 57-59 were previously cancelled.

New claims 65-70 are added and determined to be patentable.

Claims 1-56 and 60-64 were not reexamined.

*65. A method for reducing wrinkles in tissue comprising the steps of: delivering plasmonic nanoparticles to the tissue, said plasmonic nanoparticles comprising silver or gold, and exposing said delivered plasmonic nanoparticles to light at one or more wavelengths between approximately 750 to 1300 nm wherein said plasmonic nanoparticles absorb said light and emit heat at a surface of said plasmonic nanoparticle.*

*66. The method of claim 65 further comprising delivering said plasmonic nanoparticles as a component of a composition in which said plasmonic nanoparticles are present at a weight percentage of between about 2 to about 75 weight percent.*

*67. A method for resurfacing tissue comprising the steps of: delivering plasmonic nanoparticles to the tissue, said plasmonic nanoparticles comprising silver or gold, and exposing said delivered plasmonic nanoparticles to light at one or more wavelengths between approximately 750 to 1300 nm wherein said plasmonic nanoparticles absorb said light and emit heat at a surface of said plasmonic nanoparticle.*

*68. The method of claim 67 further comprising delivering said plasmonic nanoparticles as a component of a composition in which said plasmonic nanoparticles are present at a weight percentage of between about 2 to about 75 weight percent.*

*69. A method for ablating tissue comprising the steps of: delivering plasmonic nanoparticles to the tissue, said plasmonic nanoparticles comprising silver or gold, and exposing said delivered plasmonic nanoparticles to light at one or more wavelengths between approximately 750 to 1300 nm wherein said plasmonic nanoparticles absorb said light and emit heat at a surface of said plasmonic nanoparticle.*

*70. The method of claim 69 further comprising delivering said plasmonic nanoparticles as a component of a composition in which said plasmonic nanoparticles are present at a weight percentage of between about 2 to about 75 weight percent.*

* * * * *

(12) INTER PARTES REVIEW CERTIFICATE (1215th)
United States Patent (10) Number: US 6,685,730 K1
West et al. (45) Certificate Issued: Jun. 17, 2019

(54) OPTICALLY-ABSORBING NANOPARTICLES FOR ENHANCED TISSUE REPAIR

(75) Inventors: Jennifer L. West; Rebekah Drezek; Scott Sershen; Nancy J. Halas

(73) Assignee: RICE UNIVERSITY

Trial Number:

IPR2017-00046 filed Oct. 7, 2016

Inter Partes Review Certificate for:

Patent No.: 6,685,730
Issued: Feb. 3, 2004
Appl. No.: 10/254,233
Filed: Sep. 25, 2002

The results of IPR2017-00046 are reflected in this inter partes review certificate under 35 U.S.C. 318(b).

INTER PARTES REVIEW CERTIFICATE
U.S. Patent 6,685,730 K1
Trial No. IPR2017-00046
Certificate Issued Jun. 17, 2019

AS A RESULT OF THE INTER PARTES REVIEW PROCEEDING, IT HAS BEEN DETERMINED THAT:

Claims 57-59 are cancelled.

\* \* \* \* \*